United States Patent [19]

Scribner

[11] 4,399,290
[45] * Aug. 16, 1983

[54] OPTICALLY ACTIVE TERT-ALKYL 7-(2-OXO-5-CARBONYLOXYPYR-ROLIDINYL)HEPTANOATES

[75] Inventor: Richard M. Scribner, Wilmington, Del.

[73] Assignee: E. I. Du Pont de Nemours and Company, Wilmington, Del.

[*] Notice: The portion of the term of this patent subsequent to Mar. 23, 1999, has been disclaimed.

[21] Appl. No.: 328,842

[22] Filed: Dec. 9, 1981

Related U.S. Application Data

[62] Division of Ser. No. 189,061, Sep. 22, 1980, Pat. No. 4,321,201.

[51] Int. Cl.³ .......................................... C07D 207/28
[52] U.S. Cl. .................................................. 548/534
[58] Field of Search ......................................... 548/534

[56] References Cited

U.S. PATENT DOCUMENTS 3,965,143  6/1976  Collins et al. ...................... 424/317

Primary Examiner—Jane T. Fan
Attorney, Agent, or Firm—James A. Costello

[57] ABSTRACT

Optically active tert-alkyl 7-2(oxo-5-carbonyloxypyrrolidinyl)heptanoates and their preparation by reaction of racemic tert-alkyl 7-(2-oxo-5-carboxypyrrolidinyl)-heptanoate with an optically active amine to form resolved d or l amine salts which are then reacted with acid to form resolved acid intermediates. Esterification of these acid intermediates produces resolved d or l esters which are useful to make optically active 8-aza-prostanoids having biological activity.

6 Claims, No Drawings

OPTICALLY ACTIVE TERT-ALKYL 7-(2-OXO-5-CARBONYLOXYPYRROLIDINYL)-HEPTANOATES

CROSS-REFERENCE TO RELATED APPLICATION

This is a division of copending patent application bearing U.S. Ser. No. 189,061, filed on Sept. 22, 1980, now U.S. Pat. No. 4,321,201.

BACKGROUND OF THE INVENTION

This invention concerns optically active (resolved) tert-alkyl pyrrolidinyl heptanoate intermediates which are useful for making biologically active 8-azaprostanoids.

There is relatively little art concerned with optically active 8-azaprostanoids. U.S. Pat. No. 4,113,873 (Himizu) discloses the laevo 15α-isomer of

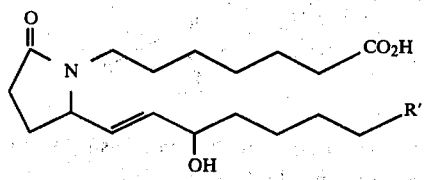

where R' is ethyl or n-propyl, or a pharmaceutically acceptable salt thereof. Also described is a process for preparing said isomer starting with the aldehyde:

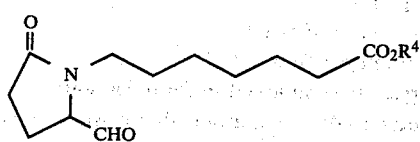

where $R^4$ is lower alkyl. The optically-active (d and l) isomers of this aldehyde are prepared by several reactions starting from d- or l-5-hydroxymethyl-2-pyrrolidone.

U.S. Pat. No. 4,177,346 (Nelson) discloses

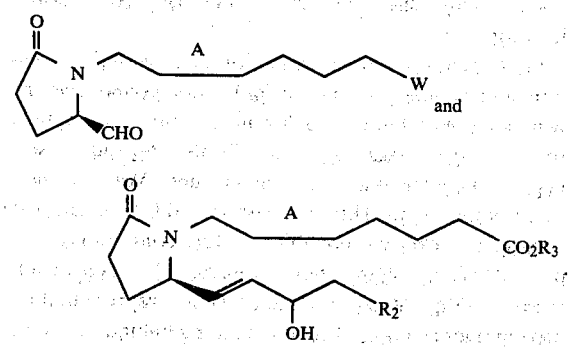

where A is a single or cis double bond. W is a tetrazol, $R_3$ is H, or alkyl of 1 to 5 carbons, and $R_2$ is phenyl. This patent discloses optically active 8-azaprostanoids:

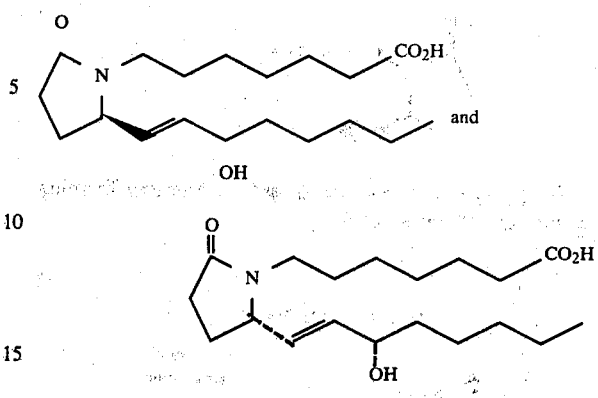

and their preparation from d or l-pyroglutamic acid. The synthetic sequence is similar to that used in the Himizu patent in that it also goes through the optically-active 5-hydroxymethyl-2-pyrrolidone.

U.S. Pat. No. 3,975,399 (De Franco and Scribner) describes various 8-azaprostanoids but does not discuss either stereoisomers or optical activity of any of the prostanoids or their intermediates. The racemic 8-azaprostanoids of the patent do not have the optical activity of the 8-azaprostanoids described herein, nor do they possess the biological properties which are a concomitant of said optical activity.

General methods for resolving racemates are discussed in the literature, for example, in "Advanced Organic Chemistry", Fieser and Fieser, Reinhold Publishing Company, 1961, pages 85 to 89; and "Organic Chemistry", Cram and Hammond, 2nd edition, 1964, McGraw-Hill, pages 174 to 176.

SUMMARY OF THE INVENTION

This invention relates to optically active tert-alkyl 7(2-oxo-5-carbonyloxypyrrolidinyl)heptanoates of the formula:

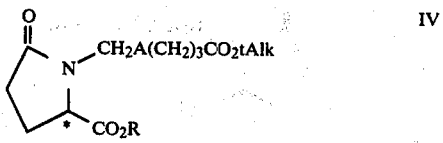

wherein the asterisk means that one enantiomer is predominant; A is $CH_2CH_2$, $CH=CH$ (cis or trans); or $C\equiv C$; tAlk is a tert-alkyl of 4 to 7 carbons; and R is H, alkyl of 1 to 4 carbons, or a protonated optically-active amine. The preferred compounds of this invention are those where Alk is butyl (Bu) or amyl (Am), A is $CH_2CH_2$, and R is H, $CH_3$ or a protonated optically-active amine, especially where the amine is d or l α-methylbenzylamine or d or l ephedrine. Enantiomers are optical isomers related as object and nonsuperimposable image.

This invention also concerns a process for preparing the optically active tert-alkyl heptanoates described above. The process comprises the steps, in sequence, of (i) reacting racemic carboxylic acids of the formula

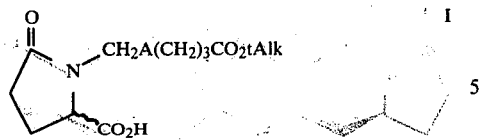

with optically active (d or l) amines, thereby forming amine salts of the formula

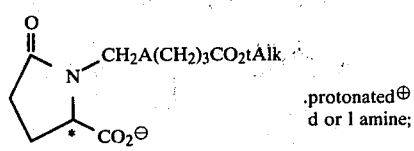

(ii) separating amine salts II from the diastereoisomeric amine salt byproducts; (iii) reacting amine salts II with mineral acids, thereby forming corresponding d or l carboxylic acids of the formula

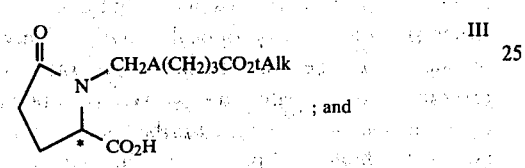

(iv) reacting the d or l carboxylic acids with an esterification agent, thereby forming compound IV of the invention wherein R is alkyl of 1 to 4 carbons.

DETAILS OF THE INVENTION

The reaction sequence described above employs racemic carboxylic acids, I, as the starting reagent. It will be appreciated by one skilled in the art that one method for making acids, I, (and the preferred method herein) is by hydrolyzing the corresponding racemic tert-alkyl 7-(2-oxo-5-alkoxycarbonylpyrrolidinyl)heptanoate diesters:

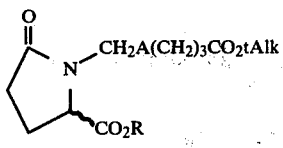

Optically active esters, IV, where R is alkyl of 1 to 4 carbons, can be employed to make optically active 8-azaprostanoids by reducing them to the optically active d or l tert-alkyl 7-(2-oxo-5-formylpyrrolidinyl)heptanoate:

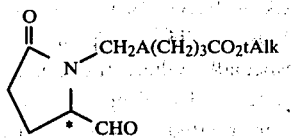

Surprisingly, reduction of optically active esters, IV, where R is alkyl of 1 to 4 carbons, does not cause racemization of the resulting aldehydes. Furthermore, these optically active aldehydes can be treated with dialkyl phosphonates of the formula:

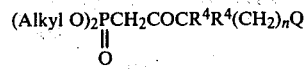

where Alkyl is 1 to 4 carbons, to give optically active 8-azaprostanoid ketones of the formula

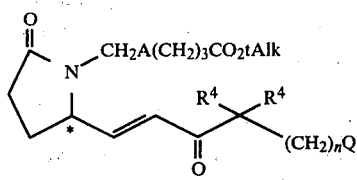

which in turn can be reduced, e.g., by a borohydride reducing agent, to optically active 8-azaprostanoids of the formula:

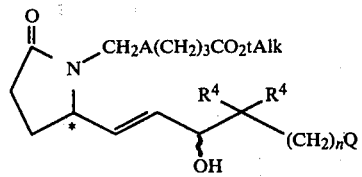

and tAlk converted to $R^3$ by hydrolysis, esterification, salt formation, and the like, wherein $R^3$ is H, aliphatic-, branched-, or cycloalkyl of 1 to 12 carbons, physiologically acceptable metal cation, or physiologically acceptable amine salt cation;

A is as described above;

$R^4$ is H, $CH_3$ or $CF_3$;

Q is $CH_3$ or $CF_3$; and n is an integer from 3 to 7.

Asterisks are employed in formulas set out herein to designate chiral carbon atoms that exist, by virtue of a resolution step, in one or predominantly one of two possible absolute configurations. That is: one isomer is present in enantiomeric excess comprising from slightly more than 50% up to 100% of the total amount of compound. Compounds having these chiral carbon atoms in one, or predominantly one, configuration are referred to as being "optically active" because at least at certain wavelengths these compounds rotate the plane of polarized light.

Generally, the sign and magnitude of the optical rotation will depend on the particular compound and the wavelength of light used for measurement of optical rotation; to a lesser degree it will also depend on solvent, concentration, and temperature. Wavey lines, representing bonds between carbon and OH, mean that a mixture of the two possible absolute configurations is present. Wedge-shaped bonds represent bonds protruding out of the plane of the paper. Bonds represented by broken lines represent bonds extending behind the plane of the paper.

The process of this invention is characterized by employing tert-alkyl ester reaction intermediates. The initial reactant is the racemic diester

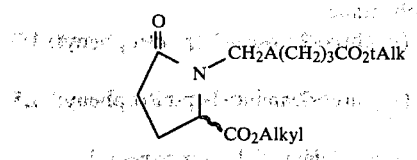

This diester is hydrolyzed by sequential treatment with aqueous base and then dilute mineral acid to give tert-alkyl ester/carboxylic acid, I, in high yield because of the combined effects of the high reactivity of the 5-carboalkoxy groups of the diester and the resistance toward saponification of the tert-alkyl ester functionality.

The advantage of the tert-alkyl ester functionality as a protecting group for the C-1 carboxyl group later is evident because optically active ester, IV, where R is alkyl of 1 to 4 carbons, is reduced selectively to the optically active tert-alkyl 7-(2-oxo-5-formylpyrrolidinyl)heptanoate without changing the C-1 functionality.

In the following Columns A and B, the racemic esters of Column A, prepared as described in U.S. Pat. No. 3,975,399 can be hydrolyzed to the racemic tert-alkyl ester acids I of Column B. Compounds identified by the same lower case letter, e.g., a, b, c . . . , belong to the same series of reactions. For example, racemic diester (a) of Column A affords racemic ester acid (a) of Column B, etc.

The racemic acids of Column B can be treated according to the process of this invention, Step (i), with 1 molar equivalent of an optically-active amine to form a d- or l-enriched amine salt. By suitable choice of solvent these d- or l-enriched salts can usually be obtained as crystalline solids, which can readily be separated from the dissolved diastereoisomeric salts. Typical solvents include ether, ethyl acetate, acetone, ethanol, 1-propanol, isopropanol and mixtures thereof.

Column A

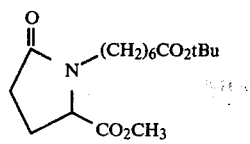 (a)

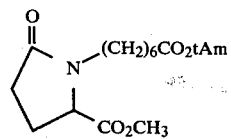 (b)

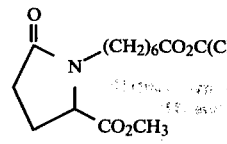 (c)

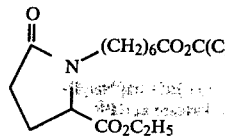 (d)

-continued
Column A

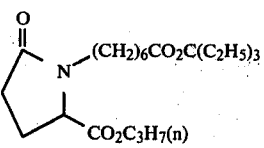 (e)

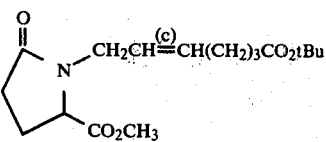 (f)

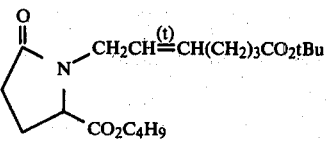 (g)

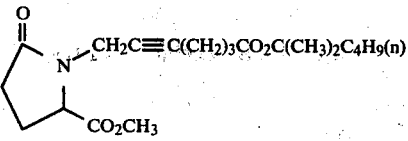 (h)

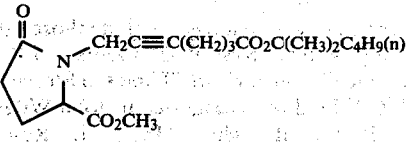 (i)

Column B
(Compound I)

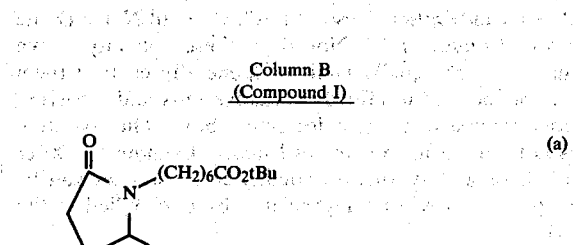 (a)

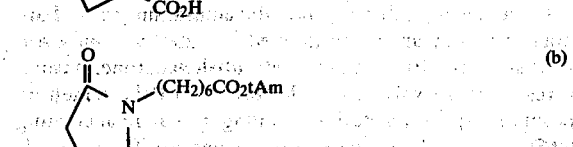 (b)

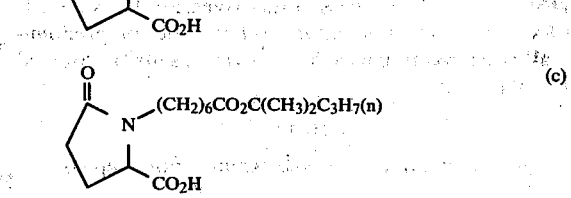 (c)

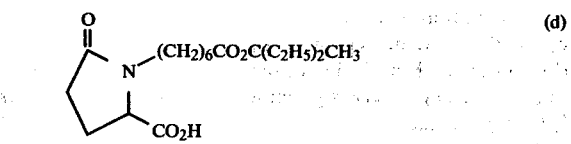 (d)

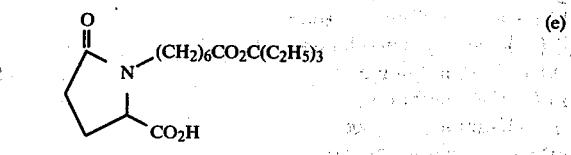 (e)

-continued
Column B
(Compound I)

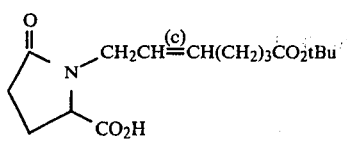
(f)

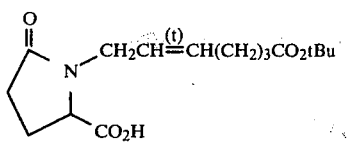
(g)

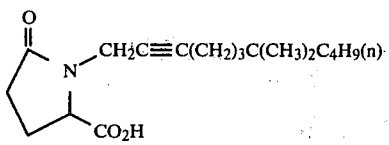
(h)

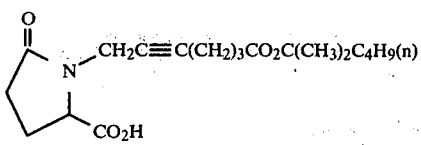
(i)

Typical optically-active amines include those listed in Column C; See Wilen, "Resolving Agents and Resolutions In Organic Chemistry", in "Topics in Stereochemistry", Vol. 6, Edited by Allinger et al, John Wiley and Sons, Inc., 1971, and Wilen, "Tables of Resolving Agents and Optical Resolutions", Univ. of Notre Dame Press, London, 1972. Not all of these optically active amines work equally well, but generally each of them can be induced to afford crystalline salts under solvent conditions such as those described above. The invention is not limited to the amines listed in Column C. Other alkaloids and synthetic optically-active amines can be employed as will be appreciated by one skilled in the art.

Once the crystalline carboxylic acid-amine salts II are obtained, they are recrystallized repeatedly from a solvent such as ethyl acetate, acetonitrile, acetone, or mixtures of these solvents with ether, until their melting point and specific rotations no longer change according to Step (ii) of the process of this invention. This affords salts of the optically-active acids in one, or predominantly one, enantiomeric form. Typical salts II are listed in Column D.

Column C

Representative Resolved Amines For Step (i)

(a) (−)brucine
(b) (−)cinchonidine
(c) (+)dehydroabietylamine
(d) (+)α-(1-naphthyl)ethylamine
(e) (−)α-(1-naphthyl)ethylamine
(f) (+)ephedrine
(g) (−)ephedrine
(h) (+)α-methylbenzylamine
(i) (−)α-methylbenzylamine
(j) (+)2-aminobutane
(k) (−)2-aminobutane
(l) (+)2-amino-1-butanol
(m) (−)2-amino-1-butanol
(n) (+)2-aminoheptane
(o) (−)2-aminoheptane
(p) (+)threo-2-amino-1-(p-nitrophenyl)-1,3-propanediol
(q) (−)threo-2-amino-1-(p-nitrophenyl)-1,3-propanediol
(r) (+)threo-2-amino-1-phenyl-1,3-propanediol
(s) (−)threo-2-amino-1-phenyl-1,3-propanediol
(t) (+)amphetamine
(u) (−)amphetamine
(v) (+)arginine
(w) (+)p-bromo-α-phenethylamine
(x) (−)p-bromo-α-phenethylamine
(y) (−)cinchonine
(z) (+)deoxyephedrine
(aa) (+)threo-2-(N,N-dimethylamino)-1-(p-nitrophenyl)-1,3-propanediol
(bb) (−)threo-2-(N,N-dimethylamino)-1-(p-nitrophenyl)-1,3-propanediol
(cc) (+)α-fenchylamine
(dd) (−)α-fenchylamine
(ee) (−)menthylamine
(ff) (+)α-methylbenzylisothiouronium acetate
(gg) (−)α-methylbenzylisothiouronium acetate
(hh) (+)α-methyl-p-nitrobenzylamine
(ii) (−)morphine
(jj) (+)α-(2-naphthyl)-ethylamine
(kk) (−)α-(2-naphthyl)-ethylamine
(ll) (+)norepinephrine
(mm) (−)norepinephrine
(nn) (+)pseudoephedrine
(oo) (−)pseudophedrine
(pp) (+)quinidine
(qq) (−)quinine
(rr) (−)strychnine
(ss) (+)yohimbine Column D
Representative Amine Salts II

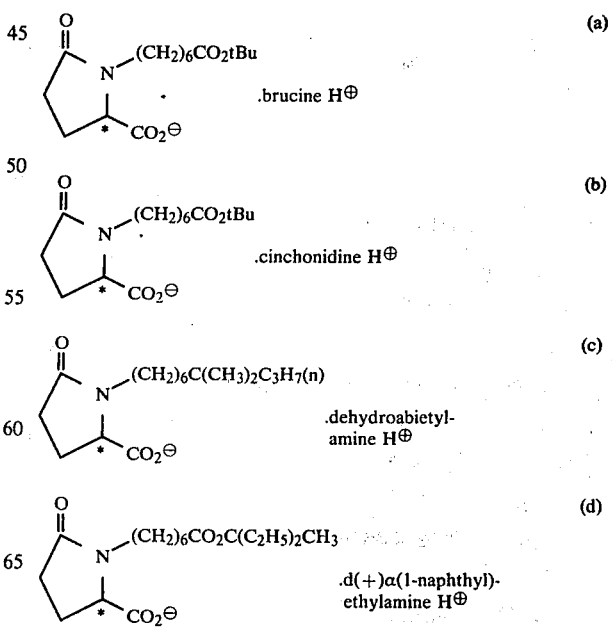

-continued
Column D
Representative Amine Salts II

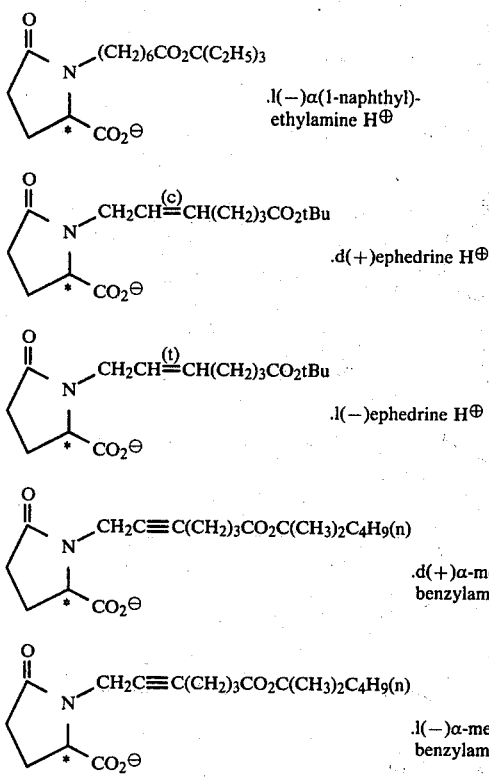

Treatment of the salts of Column D with dilute aqueous mineral acid such as hydrochloric acid or sulfuric acid, according to process Step (iii), affords the optically-active carboxylic acids of Column E. Some of the salts of Column D will afford d acids, some will afford l acids. If a given optically-active amine affords a crystalline salt containing the undesired enantiomer of a given acid, the remaining salt in the mother liquor will, of course, contain the other enantiomer of the acid.

Esterification of the optically-active acids of Column E, according to Step (iv) of the process of this invention, employing, for instance, a diazoalkane, affords optically-active esters of this invention exemplified in Column F.

The optically-active esters of Column F can then be reduced to optically-active aldehydes of Column G by the action of $NaAl(OCH_2CH_2OCH_3)_2H_2$. These optically-active aldehydes are useful precursors to the optically active 8-azaprostanoids.

Column E
(Acids III, d or l)

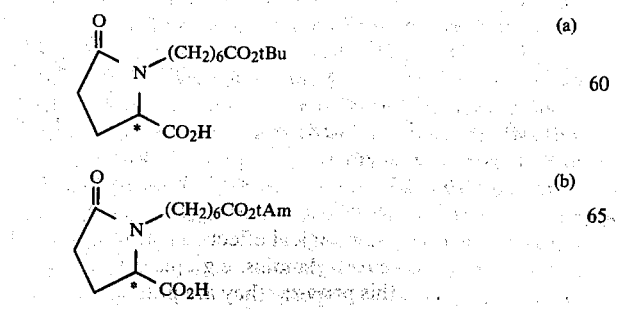

-continued
Column E
(Acids III, d or l)

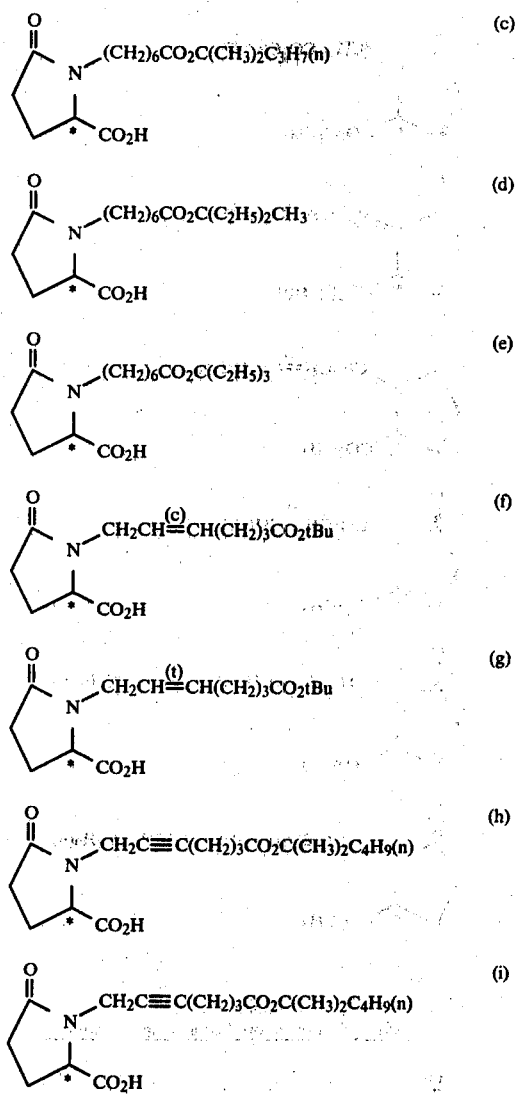

Column F
(Esters IV, d or l)

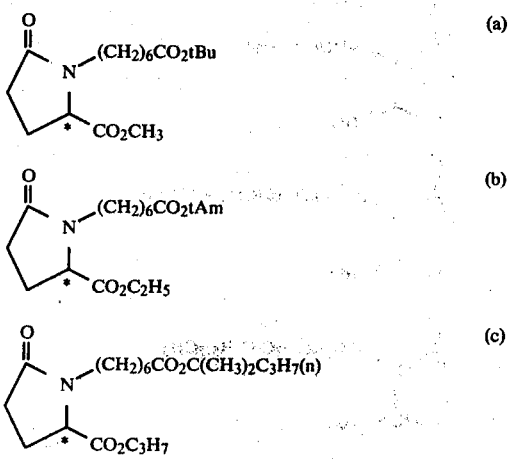

Column F
(Esters IV, d or l)

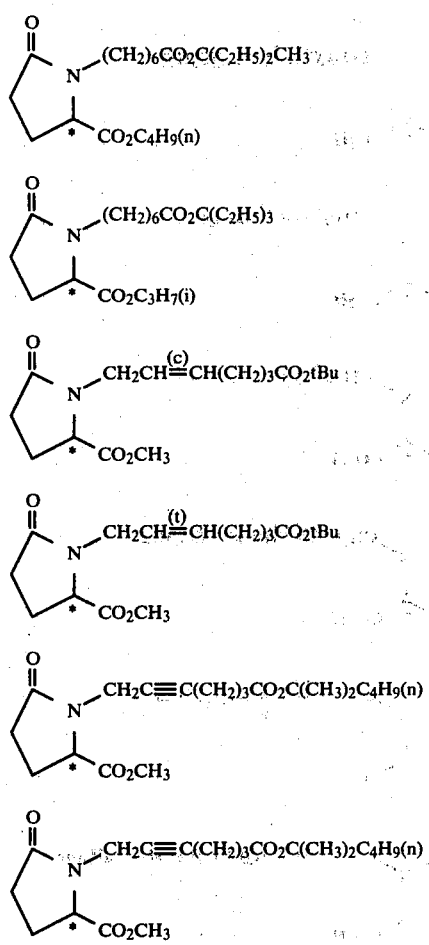

Column G
Aldehyde Precursors For 8-Azaprostanoids

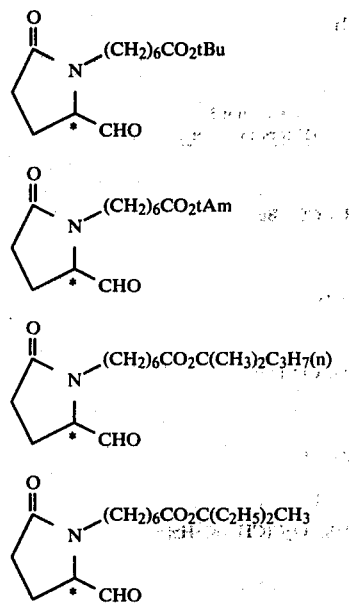

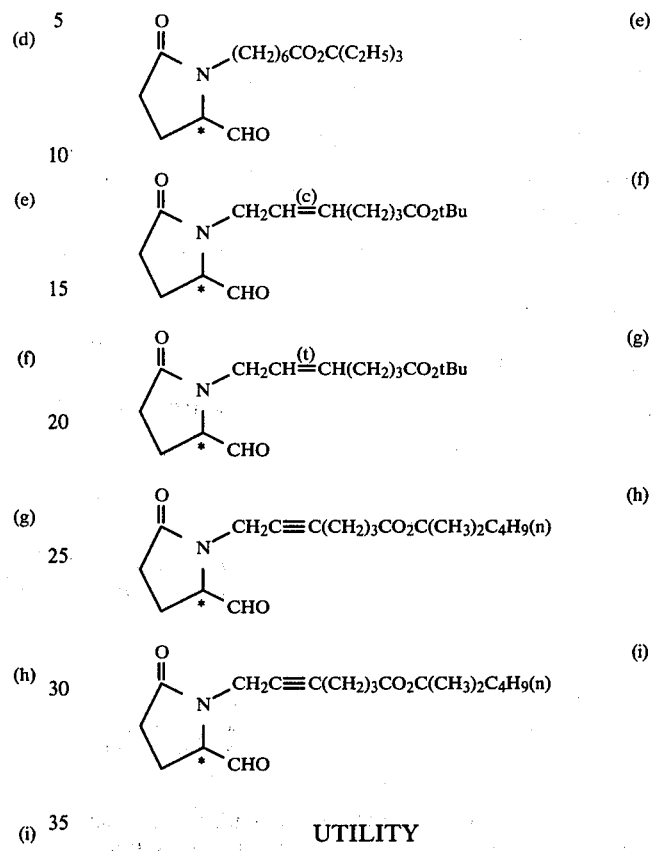

UTILITY

The optically-active intermediates of this invention are useful as precursors to optically-active 8-azaprostanoids which in turn have value as drugs and diagnostic agents. For example, the 8-azaprostanoids can be used to prepare gastric cytoprotective agents which, because they protect the mucosa of the stomach and small intestine, are of potential value in hastening the healing of peptic ulcers, or for treating inflammatory bowel diseases, such as colitis, or preventing ulcerative changes in the gastro-intestinal tract caused by non-steroidal antiinflammatory agents.

The advantages of having available different optical forms of the 8-azaprostanoids lies in differences in the kind of biological activity exhibited by these different forms. For example, some of the optical forms (or optical isomers) of the 8-azaprostanoid esters and acids derived from the optically-active intermediates of this invention are potent as cytoprotective agents in experimental animals, being several times more potent on a mg/kg basis than the racemic or optically-inactive forms of these 8-azaprostanoid esters and acids.

Some of the optically-active esters and acids, especially the acids, are potent inhibitors of histamine-induced bronchoconstriction, as a measure of potential anti-asthma activity. However, some of the optical isomers which have relatively low potencies in cytoprotection or bronchodilation tests exhibit prostaglandin-antagonism activity. That is, these optical isomers can inhibit some of the biological effects ordinarily brought about by natural prostaglandins, e.g., prostaglandin $E_1$, and by virtue of this property they are potentially useful as reagents for biochemical research, or as medical diagnostic agents or as anti-diarrheal agents.

One important aspect of the process of this invention that distinguishes it from other processes that have been used to prepare 8-azaprostaglandins having natural (R) configurations at C-12, is that it affords both natural (R) and unnatural (S) forms from readily available starting materials. As mentioned above, some of the C-12 unnatural isomers are relatively weak as prostaglandin mimics but they are more effective as prostaglandin antagonists. Table 1 summarizes various cytoprotection data.

The data of Table 1 are from tests similar to one described by Robert [U.S. Pat. No. 4,097,603 (1978)] in which fasted, male rats were treated with 8-azaprostanoids orally. Then, at various times later they were treated orally with 1.0 ml of absolute ethanol. The rats were sacrificed after ethanol administration and the stomachs were removed, inspected, and rated. The $ED_{50}$ values of Table 1 represent the doses of 8-azaprostanoids that gave 50% protection from the necrosis and inflammation of the stomach caused by ethanol. For comparison, values are given for the natural prostaglandin, $PGE_1$, and for racemic 7-[2-oxo-5(4,4-difluoro-3-hydroxy-1n-dec-1(E)-enyl)-1-pyrrolidinyl]heptanoic acid, which is identified in Table 1 as compound 8. The corresponding racemic tert-butyl ester is identified as 7. The structures of 7 and 8, each of which is a mixture of 4 optical isomers, are as follows:

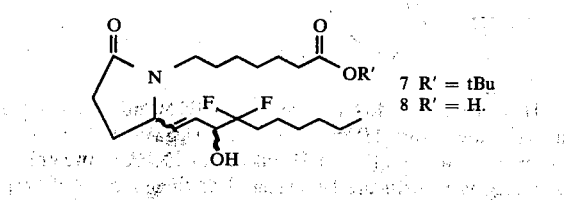

7 R' = tBu
8 R' = H.

TABLE 1

| Compound | Example No. | Percent Protection, 2 mg/kg 1 hr* | $ED_{50}$ mg/kg at Peak Time** | Peak Time** |
|---|---|---|---|---|
| $PGE_1$ | | — | .011 | 5 min |
| 7 | | 32 | | |
| 7l(15R,S) | 1C | 59 | | |
| 7d(15R,S) | 1C | −5 | | |
| 7l(15R) | 1D | 59 | | |
| 7l(15S) | 1D | 9 | | |
| 8 | — | 91 | .0035 | 15 |
| 8l(15R) | 1E | — | .0007 | 15 |
| 8l(15S) | 1E | — | .010 | 15 |

*"1 hr" refers to the 1 hour interval between administration of compound and subsequent administration of ethanol.
**"Peak Time" refers to the interval between administration of compound and administration of ethanol at which greatest protection is observed.

Some differences in biological activities of the racemic forms and different optical isomers of these 8-azaprostanoids can be seen in the data presented in Table 1. For example, optical isomer 8l(15R) is more potent as a cytoprotective agent than its racemic form 8. On the other hand, optically active ester 7d(15R,S) is less potent than its racemic form 7. In other tests, optically active ester 7d(15R,S) was more potent than 7 as an antagonist of $PGE_1$ in in vitro tests on rat stomach strips.

EXAMPLES

The following Examples illustrate the invention. Temperatures are in degrees Celsius.

EXAMPLE 1 rac tert-Butyl 7-[2-Oxo-5-carboxy-1-pyrrolidinyl]heptanoate (2).

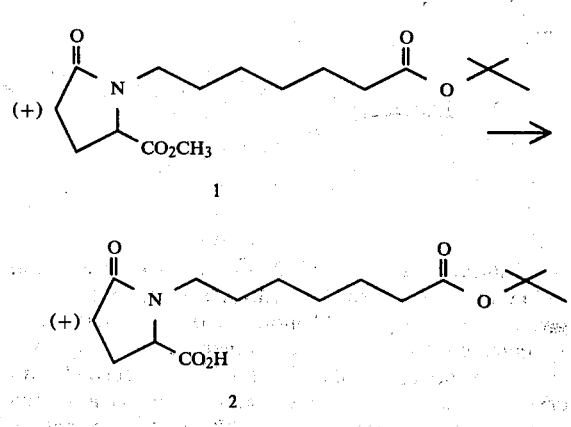

The compound, rac-tert-butyl 7-(2-oxo-5-methoxycarbonyl-1-pyrrolidinyl)heptanoate, (1) (32.7 g, 0.1 mole) which had been purified by distillation through a wiped-film molecular still, was dissolved in 60 ml of methanol and, with stirring and cooling so that the reaction mixtures stayed at 15±3°, 1.0 N NaOH was added dropwise. Then 90 ml of the caustic had been added, 3 drops of a 1% phenolphthalein indicator solution was added and enough additional caustic was added until a slight pink color persisted for 10 min. A total of 93.5 ml of 1 N NaOH was thus used. The mixture was concentrated under vacuum, mixed with 200 ml of water, and the water solution washed twice with ether, which was discarded. The aqueous solution was cooled in an ice bath and treated with 110 ml of 1.0 N HCl dropwise. Extraction with ether, drying over $MgSO_4$, and evaporation of the ether, gave 28 g (89%) of white crystalline racemic acid 2, m.p., 49° to 51°. For a sample prepared similarly: Anal. Calcd. for $C_{16}H_{27}NO_5$: C, 61.32; H, 8.68; N, 4.47; Found: C, 60.86; H, 8.52; N, 4.80.

Similarly, 65.6 g of crude racemic diester 1 that had not been previously purified by distillation was saponified in 80 ml of methanol by slow addition of 1.0 N NaOH at 35° over 2 hrs. The racemic acid 2 was isolated similarly and amounted to 51 g, m.p. 48° to 50°. This represents a significant simplification of the process used for preparing acid 2 because it eliminates the need for molecular distillation of the crude diester 1 obtained as described in U.S. Pat. No. 3,975,399.

Steps (i) and (ii) Of Process

Salts of optically-active acids 2l and 2d with optically-active amines l(−)2-methylbenzylamine and d(+)2-methylbenzylamine (3l and 3d)

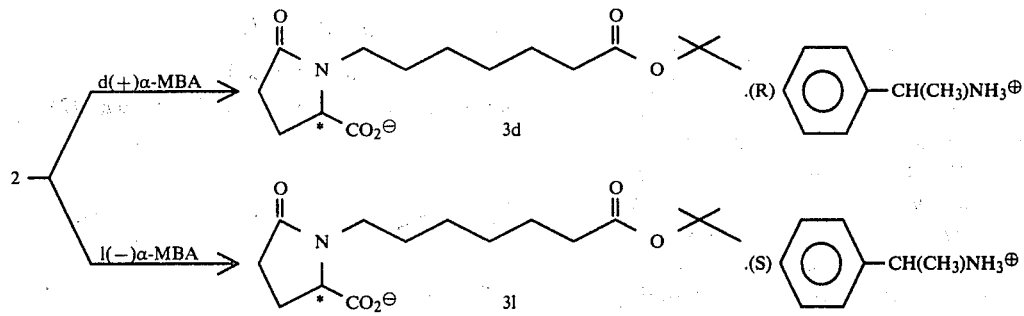

A solution of 66.37 g (0.212 mole) of racemic acid 2 in 212 ml of ether was stirred with ice cooling under nitrogen while 25.66 g (0.212 mole) of d(+)-α-methylbenzylamine diluted to 50 ml with ether was added quickly from a dropping funnel. The mixture was seeded with crystals of d(+) amine salt (obtained earlier) and stirred at room temperature for about 23 hrs. The crystalline solid was collected under nitrogen (the wet salt is hygroscopic, the pure salt is not), affording 24.9 g of salt 3d. This salt was recrystallized from 50 ml of ethyl acetate, affording 20.3 g of pure salt 3d, m.p. 100° to 102°.

The ethyl acetate and ether filtrates from above were combined, cooled in ice, and treated with 125 ml of 2 N HCl with stirring. The organic layer was separated, washed with two 75-ml portions of 1 N HCl, washed twice with saturated NaCl, and dried over Drierite. Evaporation of the solvent gave 51.96 g of acid 2 as an oil enriched in one enantiomer. This oil was dissolved in 200 ml of ether, and treated with 20.1 g of l(−)-α-methylbenzylamine in 50 ml of ether at 0°. The mixture was seeded, kept at 0° for 1 hr, and filtered, giving 20.7 g of the salt 3l, which was recrystallized from 40 ml of ethyl acetate to give 15.4 g of salt 3l, m.p. 100° to 103°.

The combined ether and ethyl acetate filtrates from precipitation of the salt 3l were treated with HCl as in the previous paragraph and the crude acid 2 obtained was treated with one equivalent of d(+)α-methylbenzylamine, etc., as above, to give in a total of three cycles 30.4 g of recrystallized salt 3d. Two cycles gave a total of 25.4 g of recrystallized salt 3l.

Very pure samples of both salts, prepared similarly but recrystallized several times from ethyl acetate, had m.p.'s of 101° to 103° (mixed m.p.'s 73° to 90°). For salt 3d: Anal. Calcd. for $C_{24}H_{38}N_2O_5$: C, 66.23; H, 8.81; N, 6.45; Found: C, 66.40; H, 8.74; N, 6.40.

Specific rotation of the optically-active salts 3d and 3l did not change significantly after two crystallizations from ethyl acetate (c=3.33, ethanol):

|  | 3d | 3l |
|---|---|---|
| $[\alpha]_D$ | −2.8° | +2.3° |
| $[\alpha]_{365}$ | −50.6° | +49.0° |

Step (iii) of Process d(+) tert-Butyl 7-[2-Oxo-5-carboxy-1-pyrrolidinyl]heptanoate (2d) and l(−) tert-Butyl 7-[2-Oxo-5-carboxy-1-pyrrolidinyl]heptanoate (2l)

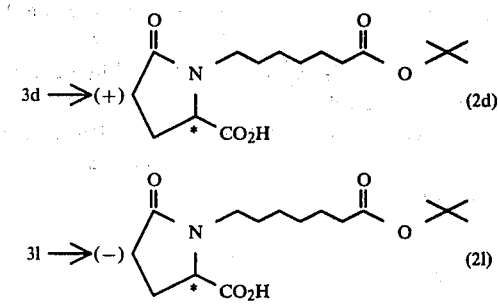

Treatment of 0.434 g of salt 3d with 50 ml of ether, 8 ml of water, and 2.0 ml of 1 N HCl gave in the ether layer after washing with 10 ml of 0.1 N HCl, and then washing with saturated NaCl and drying over MgSO4, 0.303 g (97%) of the resolved acid 2d as a colorless liquid, $[\alpha]_D$+0.9° (EtOH). Similarly, salt 3l was converted to resolved acid 2l $[\alpha]_D$−1.0° (EtOH).

Acid 2d is one, or predominantly one, enantiomer, believed to have the absolute configuration represented by 2(R), whereas acid 2l is one, or predominantly one, enantiomer believed to have the absolute configuration represented by 2(S).

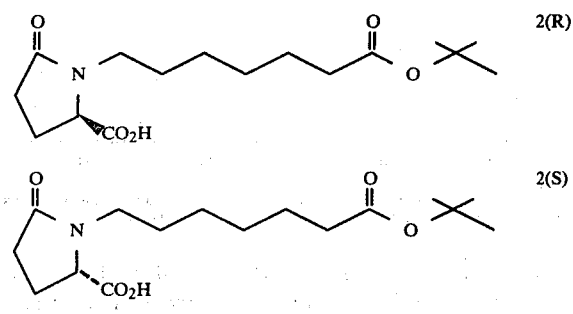

It is to be understood that the absolute configurations represented above by structures 2(R) and 2(S) and subsequently for compounds derived from these acids are based on signs of optical rotation, chromatographic behavior, and biological properties of interrelated members of the series of compounds.

Step (iv) Of Process d(+) tert-Butyl
7-[2-Oxo-5-methoxycarbonyl-1-pyrrolidinyl]heptanoate
(1d) and l(−) tert-Butyl
7-[2-Oxo-5-methoxycarbonyl-1-pyrrolidinyl]heptanoate
(1l)

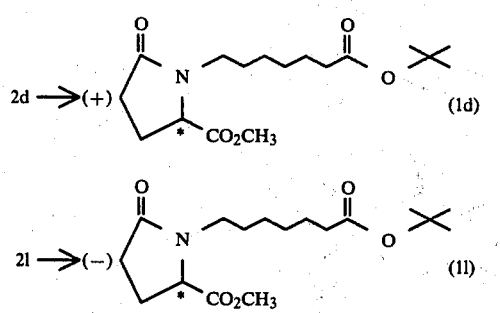

Treatment of resolved acid 2d (9.06 g), prepared similarly to that described above, with excess diazomethane in ether, gave 8.53 g of the corresponding resolved methyl ester (1d); $[\alpha]_D + 6.2°$ (±0.1°), $[\alpha]_{365} - 31.4°$ (±0.1°), (c=6.67 EtOH).

Treatment of resolved acid 2l (9.4 g) prepared in a manner similar to that described for 2d gave 8.68 g of ester 1l (EtOH); $[\alpha]_D - 6.3°$ (±0.1°), $[\alpha]_{365} + 31.5°$ (±0.1°) (c=6.67 EtOH).

Ester 1d is one or predominantly one enantiomer believed to be 1(R), whereas 1l is one or predominantly one enantiomer believed to be 1(S):

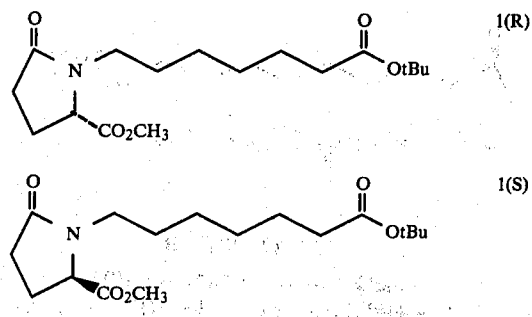

Preparation of Aldehydes l and d tert-Butyl
7-(2-Oxo-5-formyl-1-pyrrolidinyl)-heptanoate 4l and 4d

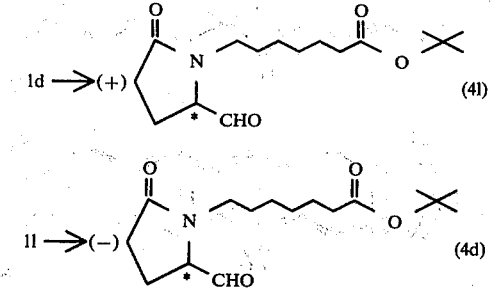

A solution of 3.27 g of resolved ester 1d in 15 ml of tetrahydrofuran (THF) was cooled to −78° and 2.5 ml of a 70% solution of sodium bis(2-methoxyethoxy)aluminum hydride in toluene (Vitride T ®) in 10 ml of THF was added dropwise with stirring. The mixture was stirred for 2.5 hrs with continued cooling, poured into about 300 ml of saturated oxalic acid solution, and extracted three times with ether. The ether was dried over CaSO4 and evaporated, giving 2.49 g (84%) of resolved aldehyde 4l as a colorless oil. The aldehyde was dried further, dehydrating the aldehydrol present, by dissolving it in toluene and removing the toluene under reduced pressure at about 50°.

Similarly, 4.9 g of resolved ester 1l in 20 ml of THF at −78° was treated with 3.8 ml of Vitride T ® solution in 15 ml of THF for 6 hrs, giving 3.91 g (71%) of resolved aldehyde 4d as a colorless oil; pmr (CDCl3, TMS) 9.58 ppm (d, J=2.5 Hz CHO, 1) ppm, and other peaks identical to those observed for the racemic (d,l) tert-butyl 7-(2-oxo-5-formyl)heptanoate.

In a modified procedure, 7.1 g (22.6 mmoles) of ester 1l in 35 ml of THF at −78° was treated dropwise with a solution of 5.2 ml of Vitride T ® in 50 ml of THF. The addition was carried out very slowly over 1.25 hrs and then the reaction mixture was kept at −78° for 5 hrs before pouring into 400 ml of water containing 15 g of oxalic acid and saturated with respect to NaCl. After 3 extractions with ether, drying the ether over MgSO4 and CaSO4, and evaporation of the ether, there was obtained the optically-active aldehyde 4d. Aldehyde 4d was then dried by evaporation of its toluene solution as described above, giving 6.9 g of aldehyde 4d as a light yellow oil, $[\alpha]_{365} + 29.4°$ (c=3.33 ethanol).

Similarly, ester 1d was treated with Vitride T ® by this modified procedure giving aldehyde 4l as a light yellow oil, $[\alpha]_{365} - 24.8$ (c=3.33 ethanol).

Optically-active aldehyde 4l is believed to be predominantly 4(R) and optically-active aldehyde 4d is believed to be predominantly 4(S):

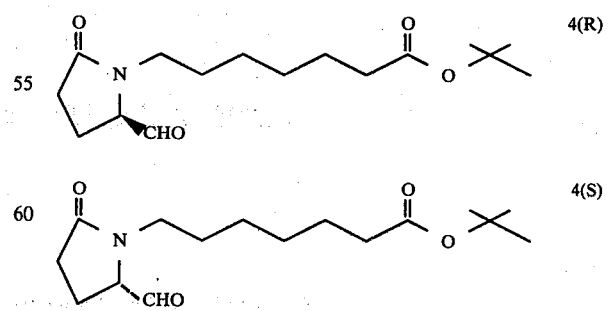

Several 8-azaprostanoids were prepared from these aldehydes according to the procedures of Examples 1A to 1F.

EXAMPLE 1A

Preparation of 8-Azaprostanoids l and d tert-Butyl 7-[2-Oxo-5-(R or S)-5-(4,4-dimethyl-3-oxo-1n-oct-1(E)-ene)-1-pyrrolidinyl]heptanoate (5l or 5d)

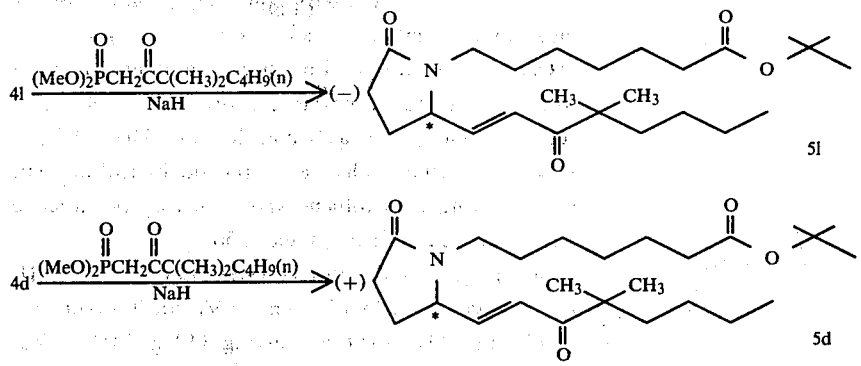

To 0.325 g (8.04 mmoles) of 59.6% sodium hydride in oil that had been washed three times with petroleum ether under nitrogen was added 50 ml of dry ethylene glycol dimethyl ether ("glyme") and then to this stirred suspension was added dropwise a solution of 2.30 g (9.2 mmoles) of dimethyl 3,3-dimethyl-2-oxoheptylphosphonate in 25 ml of glyme. The mixture was stirred for 30 min after the addition was completed, the solution of the sodium salt of the phosphonate was cooled to −40°, and then a solution of 2.49 g (8.38 mmoles) of the aldehyde 4l in 10 ml of glyme was added. The reaction mixture was kept at −40° for 10 minutes and then allowed to warm slowly to 0°, at which temperature it was kept for 40 min. A solution of 1 ml of water saturated with NH$_4$Cl was added and then the organic solvent was removed under reduced pressure. The residue was mixed with 100 ml of water and extracted three times with ether. The ether was washed with water, dried, and evaporated, giving 3.8 g of the optically-active 8-azaprostanoid ketone 5l. Purification by HPLC (2:1 ethyl acetate/hexane) gave 2.4 g of 5l (71%) in a colorless oil; HRMS:

| meas. | calcd. | assignment |
|---|---|---|
| 421.3184 | 421.3190 | $C_{25}H_{43}O_4N$ |
| 365.2577 | 365.2564 | M—$C_4H_8$ |
| 348.2543 | 348.2536 | M—$C_4H_9O$ |
| 308.1863 | 308.1860 | M—($C_4H_8$ + $C_4H_9$) |

The pmr spectrum of 5l (220 MHz, CDCl$_3$, TMS) agreed well with the assigned structure, showing an AB doublet centered at about 6.5 ppm, one pair of peaks being split further into doublets. For 5l $[\alpha]_D$ −3.2°, $[\alpha]_{405}$ = −14.6° (c = 3.33, dioxane).

Similarly, aldehyde 4d was converted to 8-azaprostanoid ketone 5d; HRMS and pmr analyses gave essentially identical results. For 5d $[\alpha]_D$ = +3.4°, $[\alpha]_{405}$ = +15.1° (c = 3.33, dioxane).

Optically-active 8-azaprostanoid ketones 5l and 5d were each predominantly one enantiomer believed to have the absolute configurations represented, respectively, by structures 5(R) and 5(S).

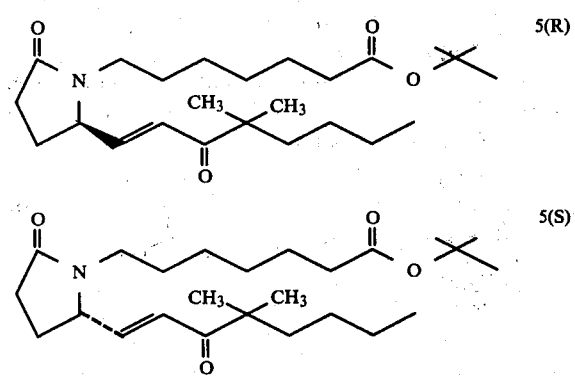

EXAMPLE 1B l and d tert-Butyl 7-[2-Oxo-5(R or S)-5-(4,4-difluoro-3-oxo-1n-dec-1(E)-ene)-1-pyrrolidinyl]heptanoate 6l and 6d

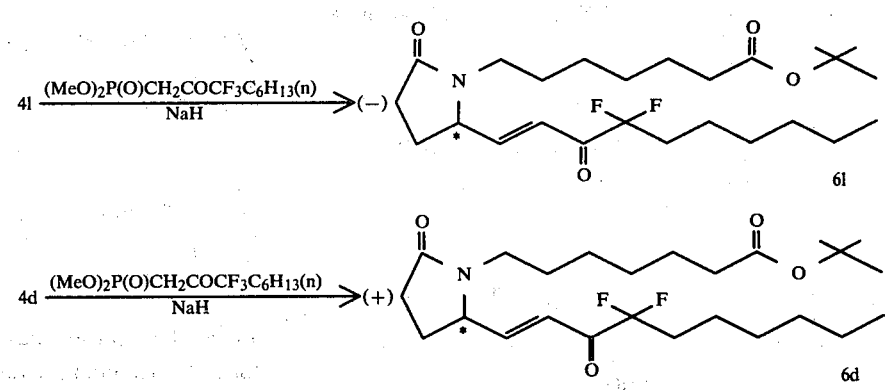

A suspension of 12.4 mmoles of NaH in glyme was prepared by washing under nitrogen 0.540 g of 55% NaH/oil with petroleum ether and then adding 20 ml of glyme. With cooling in an ice bath and with stirring, a solution of 4.25 g (14.8 mmoles) of dimethyl 3,3-difluoro-2-oxo-n-nonylphosphonate in 15 ml of glyme was added dropwise over about 15 min. The sodium salt was stirred at 0° for 5 min and then to the clear solution was added 4.1 g (13.8 mmoles) of aldehyde 4l in 15 ml of glyme. The reaction mixture was heated at reflux temperature for 1.5 hrs, cooled, and concentrated under reduced pressure at 40°. The residue was mixed with saturated $NH_4Cl$ solution and extracted with ether. The ether was dried ($MgSO_4/CaSO_4$) and evaporated, and the crude ketone 6l was purified by HPLC (EtOAc then 3:1 EtOAc/hexane). The pure, optically-active 8-azaprostanoid 6l thus obtained was a colorless oil weighing 2.77 g (49% yield); $[\alpha]_D -0.5°$; $[\alpha]_{405} -20.7°$ (c=3.33, dioxane); HMRS calcd for $C_{21}H_{33}O_4NF_2$ (m/e of M-$C_4H_9$) 401.2376; meas. 401.2401.

A suspension of 19.6 mmoles of NaH in 60 ml of glyme was prepared similarly from 0.867 g of 55% NaH/oil. This was kept at −5° to −8° while a solution of 5.89 g (20.6 mmoles) of dimethyl 3,3-difluoro-2-oxo-n-nonyl-phosphonate in 45 ml of glyme was added dropwise over 1 hour; then 6.7 g (22.6 mmoles) of aldehyde 4d in 30 ml of glyme was added all at once and the mixture was stirred at room temperature for 2 hrs. The mixture was concentrated under vacuum, mixed with 130 ml of water containing 15 g of $NH_4Cl$, and extracted with ether. The ether was dried and evaporated and the crude product was purified by HPLC (1:1 EtOAc/hexane), affording pure, optically-active 8-azaprostanoid ketone 6d (TLC, $R_f$=0.5, 1:1 EtOAc/hexane), $[\alpha]_D +1.1°$, $[\alpha]_{405} +20.8°$ (c=3.33, dioxane). The pmr spectrum confirmed the structure.

$^{19}F$ nmr spectra of samples of these two 8-azaprostanoid ketones prepared similarly showed ($CDCl_3$, F-11) proton-decoupled singlets at −107.46 ppm.

Optically active 8-azaprostanoid ketones 6l and 6d are each predominantly a single enantiomer. Their absolute configurations are believed to be as represented by structures 6(R) for 6l and 6(S) for 6d.

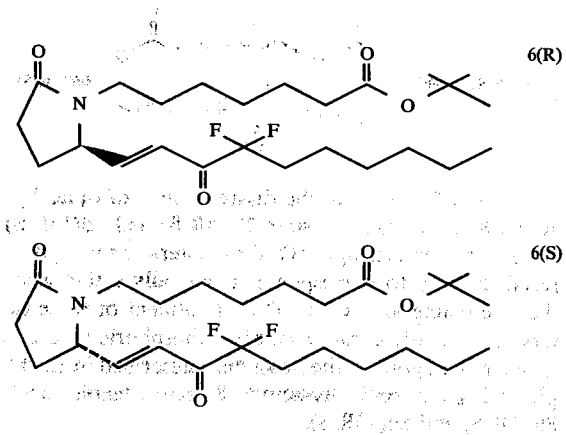

EXAMPLE 1C

Optically-active (l) tert-butyl 7-[2-oxo-5(R or S)-5-(4,4-difluoro-3(R,S)hydroxy-ln-dec-1(E)-enyl)-1-pyrrolidinyl]heptanoate[7l(15R,S)] and optically-active (d) tert-butyl 7-[2-oxo-5-(S or R)-5-(4,4-difluoro-3(R,S)hydroxy-ln-dec-1(E)-enyl)-1-pyrrolidinyl]heptanoate[7d(15R,S)]

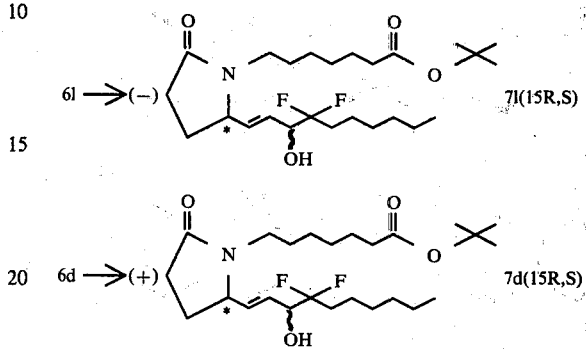

A mixture of 2.6 g of optically-active 8-azaprostanoid ketone 6l and 0.5 g of $NaBH_4$ in 50 ml of ethanol was kept at −20° for 3.3 hrs and then poured into 500 ml of saturated $NH_4Cl$ solution and extracted with ethyl acetate. The ethyl acetate extract was dried ($MgSO_4/CaSO_4$) and evaporated giving the optically-active mixture of 8-azaprostanoids 7l(15R,S). Analysis by TLC (silica gel, EtOAc) showed this to be an approximately 50:50 mixture of the two C-15 epimeric alcohol ($R_f$= ~0.5); analytical HPLC (5% ethanol in cyclopentane) showed a ratio of about 53/47 (less mobile isomer to more mobile isomer). HRMS showed a very weak 459 parent ion (M) and a stronger M-$C_4H_9$ ion $C_{21}H_{34}O_4NF_2$, calcd 402.2454, meas. 402.2483; $^{19}F$ nmr ($CDCl_3$, TMS, F-11) shows two sets (2 diastereomeric) of AB patterns (proton decoupled) with each set of peaks centered at −107.18 (weak), −109.82 (strong), −111.26 (strong), −113.92 (weak) ppm. Specific rotations for another sample prepared similarly $[\alpha]_D -11.6°$, $[\alpha]_{365} -57.9°$ (c=3.33, EtOH).

In like manner, reduction of 0.8 g of ketone 6d by 0.15 g of $NaBH_4$ in 25 ml of ethanol at −20° for 5 hrs gave the optically-active mixture of 8-azaprostanoids 7d(15R,S); HRMS identical to that of 7l(15R,S); $[\alpha]_D +11.8°$, $[\alpha]_{365} +58.4°$ (c=3.33, EtOH).

EXAMPLE 1D

Four optically-active isomers of tert-butyl 7-[2-oxo-5(R or S)-5-(4,4-difluoro-3(R or S)-3-hydroxy-ln-dec-1(E)-enyl)-1-pyrrolidinyl]heptanoate; 7l(15R), 7l(15S), 7d(15R) and 7d(15S)

Alcohols 7l(15R,S) being diastereomeric can be separated by chromatography. Likewise, alcohols 7d(15R,S) can be separated by chromatography. A particularly effective solvent system for these separations when they are carried out by HPLC on silica gel is 5% isopropyl alcohol in cyclopentane. In this manner, alcohol 7l(15R,S) can be separated into optically-active alcohols 7l(15R) and 7l(15S) and alcohol 7d(15R,S) can be separated into optically active alcohols 7d(15S) and 7d(15R). These four optically-active alcohols are predominantly single optical isomers with what are believed to be the following absolute configurations.

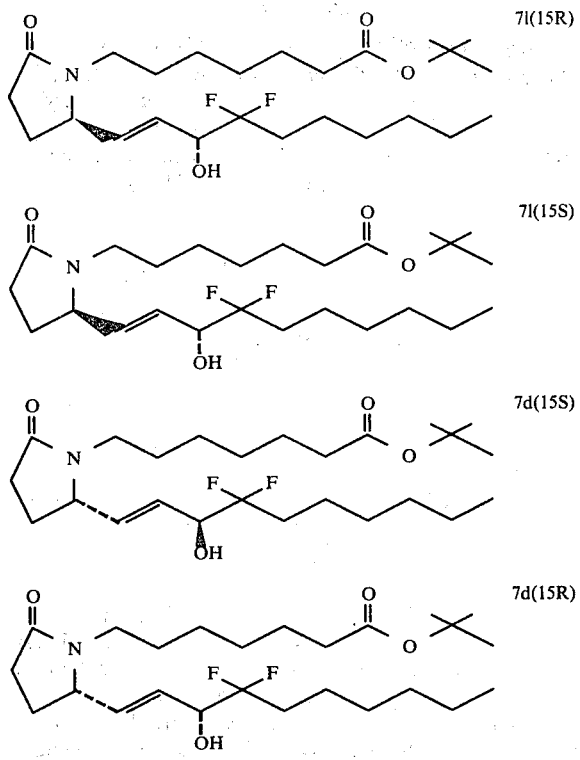

Alcohol 7l(15R) (the slower-moving diastereomer) had $[\alpha]_D+1.9°$, $[\alpha]_{365}-11.0°$ (c=3.33, ethanol); alcohol 7l(15S) (the faster-moving diastereomer) had $[\alpha]_D-29.7°$, $[\alpha]_{365}-122.4°$ (c=3.33, ethanol). Alcohol 7d(15S) (slower moving) had $[\alpha]_D-1.3°$, $[\alpha]_{365}+13.5°$ (c=3.33, ethanol) and alcohol 7d(15R) (faster moving) had $[\alpha]_D+28.0°$, $[\alpha]_{365}+114.8°$ (c=3.33, ethanol). The HRMS spectra of these four alcohols were essentially identical, and supported the molecular ion assignment $C_{25}H_{43}O_4NF_2$. The $^{19}F$ nmr (CDCl$_3$, TMS, F-11) spectra confirmed both the structure of these alcohols and the fact that the diastereomeric components had been separated since each show a single AB pattern (when proton decoupled); e.g., for 7l(15R) single peaks were found at $-107.23$ (weak), $-109.86$ (strong), $-111.37$ (strong) and $-114.01$ (weak) ppm and for 7l(15S) single peaks were found at $-107.49$ (weak), $-110.14$ (strong), $-11.38$ (strong), and $-114.04$ (weak) ppm.

EXAMPLE 1E

Four optically-active isomers of 7-[2-oxo-5(R or S)-5-(4,4-difluoro-3(R or S)-3-hydroxy-ln-dec-1(E)enyl)-1-pyrrolidinyl]heptanoic acid [8l(15R), 8l(15S), 8d(15S), and 8d(15R)]

A solution of 0.390 g of the tert-butyl ester 7 l(15R) in 2 ml of tetrahydrofuran was added with stirring to 10 ml of 85% phosphoric acid cooled in an ice bath. The ice bath was then removed and the mixture stirred at ambient temperature for about 4 hours. It was then poured into 50 cc of saturated NaCl solution and extracted three times with ethyl acetate, which was dried and evaporated. Purification of the acid thus obtained by dissolving it in 5% NaHCO$_3$ and then regenerating it by acidification, gave 0.280 g of optically active 8-azaprostanoid acid 8l(15R). This acid is one, or essentially one, optical isomer. Treatment of the other optically-active esters 7l(15S), 7d(15R), and 7d(15S) similarly with phosphoric acid gave the corresponding acids 8l(15S), 8d(15R), and 8l(15S), each being one, or essentially one, optical isomer. The absolute configurations of these optically-active acids are believed to be as indicated in the following structures.

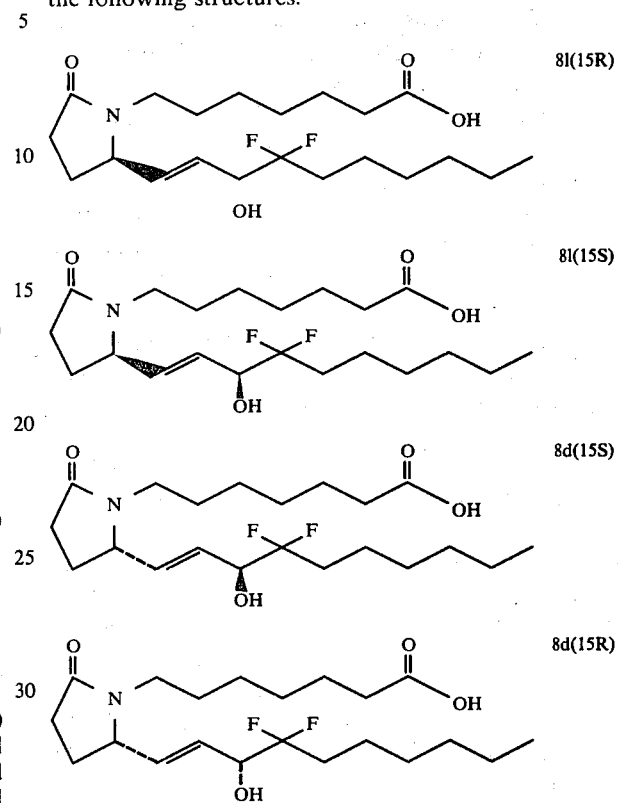

EXAMPLE 1F

Optically-active (l) 7-[2-Oxo-5(R or S)-5-(4,4-difluoro-3(R,S)hydroxy-ln-dec-1(E)-enyl)-1-pyrrolidinyl]heptanoic acid [8l(15R,S)] and optically-active (d) 7-[2-Oxo-5(S or R)-5-(4,4-difluoro-3-(R,S)hydroxy-ln-dec-1-(E)-enyl)-1-pyrrolidinyl]heptanoic acid [8d(15R,S]

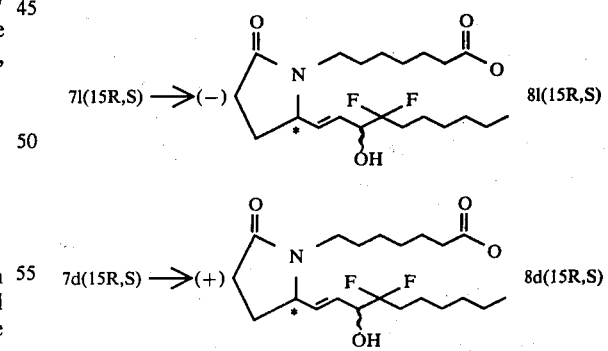

Instead of separating the diastereomers of optically-active 8-azaprostanoid esters 7l(15R,S) and 7d(15R,S) as described in Example 1D, these esters can be hydrolyzed directly to corresponding optically-active acids that are epimeric at C-15. Thus, treatment of these esters in tetrahydrofuran with 85% phosphoric acid in a manner analogous to the procedure described in Example 1E gave optically-active 8-azaprostanoid acids 8l(15R,S) and 8d(15R,S).

The embodiments of the invention in which an exclusive property or privilege is claimed are defined as follows:

1. A compound of the formula

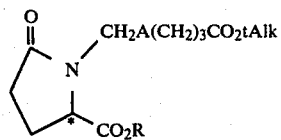

wherein the asterisk means that one enantiomer is predominant; A is CH$_2$CH$_2$, CH=CH (cis or trans); or C≡C; tAlk is a tertiary alkyl of 4 to 7 carbons; and R is a protonated optically-active amine selected from the group consisting essentially of (−)brucine, (−)cinchonidine, (+)dehydroabietylamine, (+)α-(1-naphthyl)ethylamine, (−)α-(1-naphthyl)ethylamine, (+)ephedrine, (−)ephedrine, (+)α-methylbenzylamine, (−)α-methylbenzylamine, (+)2-aminobutane, and (−)2-aminobutane.

2. A compound according to claim 1 wherein tAlk is tBu.

3. A compound according to claim 1 wherein A is —CH$_2$CH$_2$—.

4. A compound according to claim 1 wherein A is cis or trans —CH=CH—.

5. A compound according to claim 1 wherein A is —C≡C—.

6. A compound according to claim 3 wherein tAlk is tBu.

* * * * *